(12) United States Patent
Berzofsky et al.

(10) Patent No.: US 7,867,977 B2
(45) Date of Patent: Jan. 11, 2011

(54) IMMUNOGENIC PEPTIDES AND METHODS OF USE FOR TREATING AND PREVENTING CANCER

(75) Inventors: Jay A. Berzofsky, Bethesda, MD (US); Leon T. Van Den Broeke, Zoutelande (NL); Crystal MacKall, Silver Spring, MD (US); Lee J. Helman, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 86 days.

(21) Appl. No.: 12/092,449

(22) PCT Filed: Oct. 24, 2006

(86) PCT No.: PCT/US2006/041462
§ 371 (c)(1),
(2), (4) Date: Oct. 6, 2008

(87) PCT Pub. No.: WO2007/055902
PCT Pub. Date: May 18, 2007

(65) Prior Publication Data
US 2009/0117116 A1  May 7, 2009

Related U.S. Application Data

(60) Provisional application No. 60/733,319, filed on Nov. 3, 2005.

(51) Int. Cl.
*A61K 38/00* (2006.01)
(52) U.S. Cl. .............................. 514/15; 514/16; 530/328
(58) Field of Classification Search ........................ None
See application file for complete search history.

(56) References Cited

U.S. PATENT DOCUMENTS

| | | | |
|---|---|---|---|
| 4,450,150 | A | 5/1984 | Sidman |
| 5,087,616 | A | 2/1992 | Myers et al. |
| 5,225,539 | A | 7/1993 | Winter |
| 5,449,752 | A | 9/1995 | Fujii et al. |
| 5,545,806 | A | 8/1996 | Lonberg et al. |
| 5,569,825 | A | 10/1996 | Lonberg et al. |
| 5,585,089 | A | 12/1996 | Queen et al. |
| 5,639,641 | A | 6/1997 | Pedersen et al. |
| 5,693,761 | A | 12/1997 | Queen et al. |
| 5,714,352 | A | 2/1998 | Jakobovits |
| 6,265,150 | B1 | 7/2001 | Terstappen et al. |
| 2002/0197266 | A1 | 12/2002 | Debinski |

FOREIGN PATENT DOCUMENTS

| | | |
|---|---|---|
| EP | 0 239 400 B1 | 8/1994 |
| EP | 0 563 485 A1 | 10/1996 |
| GB | 2 188 638 A | 10/1987 |
| WO | WO 93/20185 A1 | 10/1993 |
| WO | WO 97/10269 A1 | 3/1997 |
| WO | WO02069900 | * 9/2002 |

OTHER PUBLICATIONS

Shapiro et al Cancer Research vol. 53 p. 5108 (1993).*
Skolnick et al. (Trends in Biotech., 18(1):34-39, 2000).*
Ahlers et al., *J. Clin. Invest.*, 108, 1677-1685 (2001).
Ahlers et al., *Proc. Natl. Acad. Sci USA*, 94, 10856-10861 (1997).
Berzofsky et al., *J. Clin. Invest.*, 113 (11), 1515-1525 (2004).
Cella et al., *J. Exp. Med.*, 184, 747-752 (1996).
Coulie et al., *Internat. J. Can.*, 50, 289-297 (1992).
Dagher et al., *Med. Pediatr. Oncol.*, 38, 158-164 (2002).
Fredericks et al., *Molecular and Cellular Biology*, 15 (3), 1522-1535 (1995).
Galili et al., *Nature Genetics*, 5 (3), 230-235 (1993).
Oh et al., *Cancer Research*, 64, 2610-2618 (2004).
Okazaki et al., *J. Immunol.*, 171, 2548-2555 (2003).
Rammensee et al., *Immunogenetics*, 41 (4), 178-228 (1995).
Rodeberg et al., *Cancer Immunol. Immunother.*, 54, 526-534 (2005).
Shapiro et al., *Cancer Res.*, 53, 5108-5112 (1993).
Van Den Broeke, *Cancer Res.*, 66 (3), 1818-1823 (2006).
Worley et al., *Cancer Res.*, 61, 6868-6875 (2001).
Berzofsky et al., "Strategies for designing and optimizing new generation vaccines," *Nat. Rev. Immunol.*, 1 (3), 209-219 (2001).
Choi et al., "Synthesis and assembly of a cholera toxin B subunit-rotavirus VP7 fusion protein in transgenic potato," *Mol. Biotechnol.*, 31 (3), 193-202 (2005).
Hudecz, "Synthesis of peptide bioconjugates," *Methods Mol. Biol.*, 298, 209-223 (2005).
Kirin et al., "Amino acid and peptide bioconjugates of copper(II) and zinc(II) complexes with a modified N,N-bis(2-picolyl)amine ligand," *Inorg. Chem.*, 44 (15), 5405-5415 (2005).
Sarobe et al., "Enhanced in vitro potency and in vivo immunogenicity of a CTL epitope from hepatitis C virus core protein following amino acid replacement at secondary HLA-A2.1 binding positions," *J. Clin. Invest.*, 102 (6), 1239-1248 (1998).
Smith et al., "Oncogenic mutations in ras create HLA-A2.1 binding peptides but affect their extracellular antigen processing," *Int. Immunol.*, 9 (8), 1085-1093 (1997).
Storkus et al., "Reversal of natural killing susceptibility in target cells expressing transfected class I HLA genes," *Proc. Natl. Acad. Sci. USA*, 86 (7), 2361-2364 (1999).

* cited by examiner

*Primary Examiner*—Sheela J Huff
(74) *Attorney, Agent, or Firm*—Leydig, Voit & Mayer, Ltd.

(57) ABSTRACT

Disclosed are immunogenic peptides, related fusion proteins, nucleic acids encoding the peptides or fusion proteins, conjugates, expression vectors, host cells, and antibodies. Also, disclosed are pharmaceutical compositions, vaccines for use in the treatment or prevention of cancer, e.g., alveolar rhabodomyosarcoma, methods of stimulating a T cell to kill a tumor cell, methods of stimulating $CD4^+$ and $CD8^+$ T cells, and methods of treating or preventing cancer are further provided herein.

17 Claims, 6 Drawing Sheets

IMMUNOGENIC PEPTIDES AND METHODS OF USE FOR TREATING AND PREVENTING CANCER

BACKGROUND OF THE INVENTION

Most tumors express mutated or inappropriately expressed, nonmutated tumor-associated antigens (TAAs) that often contain cytotoxic T lymphocyte (CTL) epitopes. Yet, the immune system often remains incapable of overtaking the growth potential of the malignant cells. Many approaches have been attempted to obtain protective and therapeutic anti-tumor immunity. However, for some of these approaches, limited success was observed (Dagher et al., *Med Pediatr Oncol* 38: 158-164 (2002); and Rodeberg et al., *Cancer Immuno Immunother* 54: 526-534 (2005)).

The present invention seeks to overcome the aforementioned problems by providing immunogenic peptides, dendritic cells presenting the immunogenic peptides, and methods of treating and preventing cancer. These and other advantages of the invention, as well as additional inventive features, will be apparent from the description of the invention provided herein.

BRIEF SUMMARY OF THE INVENTION

The present invention provides immunogenic peptides which bind to a Major Histocompatibility Complex (MHC) Class I molecule, e.g., HLA-B7. Fusion proteins and conjugates comprising at least one of the inventive immunogenic peptides described herein are also provided by the present invention.

The present invention further provides nucleic acids encoding any of the inventive immunogenic peptides or fusion proteins described herein, expression vectors comprising the nucleic acids, and host cells comprising the vectors. Isolated antibodies, or antigen binding portions thereof, that bind to any of the inventive immunogenic peptides described herein are furthermore provided by the present invention.

Pharmaceutical compositions comprising any of the inventive immunogenic peptides, fusion proteins, conjugates, nucleic acids, expression vectors, host cells, or antibodies, and a pharmaceutically acceptable carrier, are provided herein. Also, vaccines comprising any of the inventive immunogenic peptides, fusion proteins, conjugates, nucleic acids, expression vectors, or host cells are provided.

Methods of stimulating a T cell to kill a tumor cell, methods of stimulating $CD4^+$ and $CD8^+$ T cells, as well as methods of treating or preventing cancer, are further provided by the present invention.

BRIEF DESCRIPTION OF THE SEVERAL VIEWS OF THE DRAWING(S)

FIG. 1 depicts the CTL lytic activity at different effector cell:target cell (E:T) ratios. The effector cells are the CTL generated in Example 2 described herein, while the target cells are C1R-B7 cells pulsed with RS10 peptide (squares) or control peptide (triangles).

FIG. 2 depicts the CTL lytic activity at different E:T ratios. The effector cells are the CTL generated in Example 2 described herein, while the target cells are C1R-B7 cells pulsed with RS10 peptide (squares) or control peptide (triangles). Anti-HLA-B7 antibody used at 10% v/v (open circles) or 20% v/v (closed circles).

DETAILED DESCRIPTION OF THE INVENTION

Figure 1:
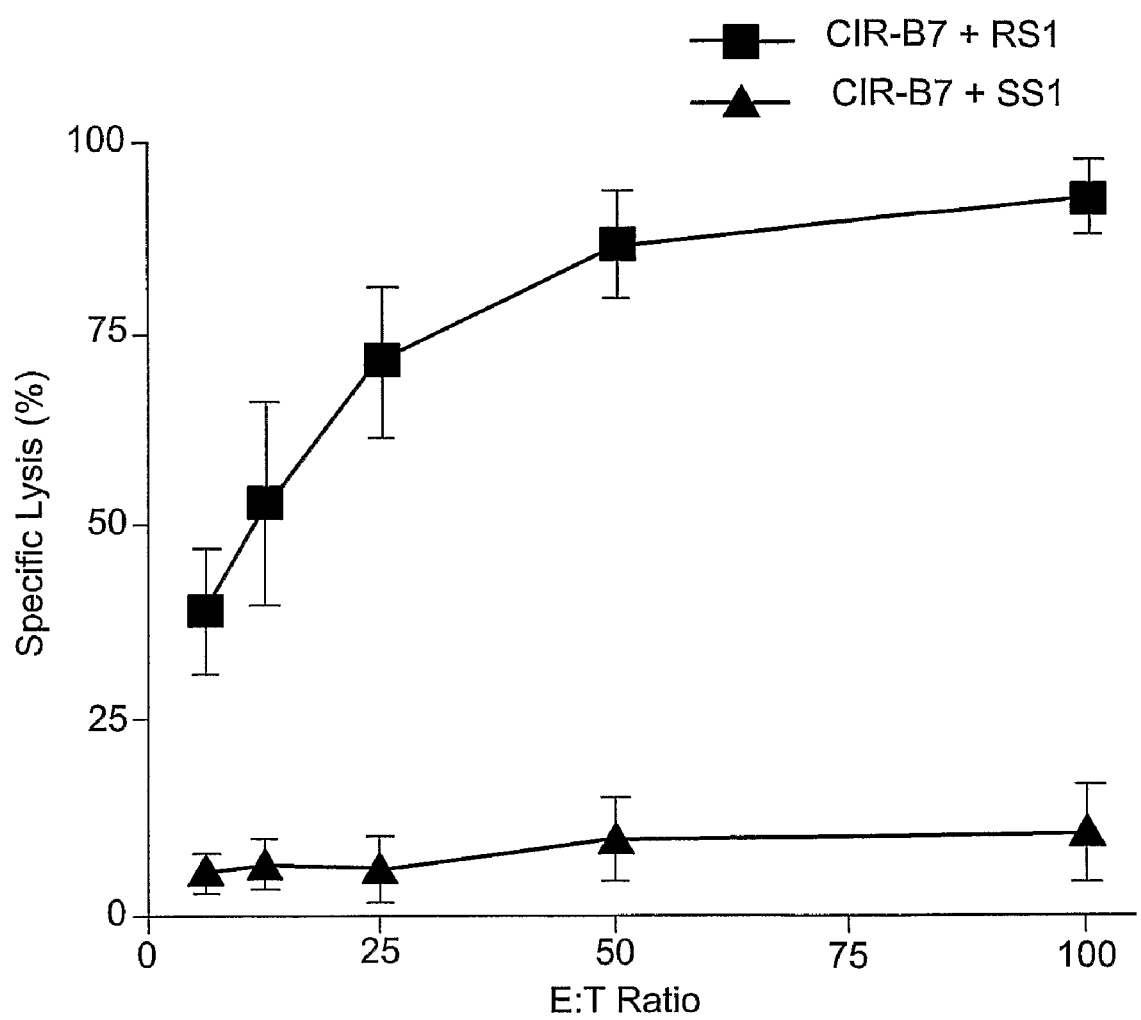

The present invention is directed to immunogenic peptides. In one embodiment, each of the peptides has an amino acid sequence based on the PAX3-FKHR fusion protein breakpoint region. The amino acid and nucleotide sequences of the PAX3-FKHR fusion protein are known in the art (SEQ ID NOs: 1 and 2, respectively) (See, for instance, Galili et al., *Nature Genetics* 5: 230-235 (1993), and Shapiro et al., *Cancer Research* 6: 5108-5112 (1993)).

In a preferred embodiment, the present inventive immunogenic peptide comprises the amino acid sequence SPQNSIRHNL (SEQ ID NO: 3), but does not consist of the amino acid sequence TIGNGLSPQNSIRHNLSL (SEQ ID NO: 4) or NPTGTIGNGLSPQNSIRHNLSLH (SEQ ID NO: 5).

In another embodiment, the present inventive immunogenic peptide comprises the amino acid sequence $SPX_1NX_2X_3RHNL$ (SEQ ID NO: 6), wherein $X_1$ is any amino acid except for Gln, $X_2$ is any amino acid except for Ser, and $X_3$ is any amino acid except for Ile.

The present inventive immunogenic peptides have one or more attractive properties. The peptides bind to an MHC Class I molecule. The MHC Class I molecule to which the peptide binds can be any MHC Class I molecule known in the art (see, for example, Janeway et al., *Immunobiology: The Immune System in Health and Disease*, 4th ed., Current Biology Publications: Garland Publishing, New York, N.Y., 1999). The MHC Class I molecule can, for example, be an MHC Class I molecule of any mammal, e.g., mouse, rat, human rabbit, etc. Suitable MHC Class I molecules include, for example, HLA-A, -B, and —C molecules, such as HLA-B7, -B8, B44, -A2, -A3, -A11, -A31, and -C1. Preferably, the MHC Class I molecule is HLA-B7. As one of ordinary skill in the art appreciates, it is possible for the inventive immunogenic peptides to bind to more than one MHC Class I molecule or to both an MHC Class I molecule and an MHC Class II molecule. Immunogenic peptides having such dual- or multi-specificities for MHC molecules are included within the scope of the invention.

Methods of determining whether a given peptide binds to an MHC Class I molecule are known in the art, and include, for instance, binding assays, such as Far Western binding assays, surface plasmon resonance binding assays, and the binding assay as illustrated in Example 1.

Desirably, the present inventive immunogenic peptides or portions thereof not only bind to an MHC Class I molecule, but also stimulate $CD8^+$ T cells, e.g., cytotoxic T lymphocytes (CTL). By "stimulate" in the context of T cells is meant activating intracellular signaling pathways in a T cell through the antigen-specific T cell receptor (TCR) expressed on that T cell, which activation leads to one or more T cell responses, such as T cell proliferation, cytolytic activity, and cytokine production, e.g., IFN-γ. Preferably, the T cells are stimulated by the present inventive peptides to kill or lyse a target cell, which presents the peptide recognized by the TCR of the T cell. Desirably, the target cell is a tumor cell. Also, in some instances, it is preferable for the peptides to stimulate $CD4^+$ T cells, in addition to $CD8^+$ T cells. Stimulation of $CD4^+$ T cells by the immunogenic peptide desirably aids a B cell mediated immune response, which includes the production of antibodies.

The immunogenic peptides of the present invention can be of any length, i.e., can comprise any number of amino acids, provided that the peptides are able to bind to an MHC Class I molecule. For example, the peptide can be 5 to 654 amino acids long, such as 5, 6, 7, 8, 9, 10, 11, 12, 13, 15, 17, 19, 20, 25, 50, 75, 100 or more amino acids in length. In a preferred embodiment, the peptide consists of 8 to 10 amino acids.

The immunogenic peptides of the present invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The present inventive immunogenic peptides can be glycosylated, amidated, carboxylated, phosphorylated, esterified, N-acylated, cyclized via, e.g., a disulfide bridge, or converted into an acid addition salt and/or optionally dimerized or polymerized, or conjugated.

When the immunogenic peptides of the present invention are in the form of a salt, preferably, the peptides are in the form of a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

The present invention also provides functional portions of the immunogenic peptides described herein. The term "functional portion" when used in reference to an immunogenic peptide refers to any part or fragment of the immunogenic peptide of the present invention, which part or fragment retains the biological (e.g., immunogenic) activity of the immunogenic peptide of which it is a part. Functional portions encompass, for example, those parts of an immunogenic peptide (the parent peptide) that retain the ability to bind to an MHC Class I molecule to a similar extent, the same extent, or to a higher extent, as the parent peptide. In reference to the parent peptide, the functional portion can comprise, for instance, about 10%, 25%, 30%, 50%, 68%, 80%, 90%, 95%, or more of the parent peptide. The functional portion can comprise additional amino acids at the amino or carboxy terminus of the portion, or at both termini, which additional amino acids are not found in the amino acid sequence of the parent peptide. Desirably, the additional amino acids do not interfere with the biological function of the functional portion, e.g., binding to an MHC Class I molecule, stimulation of $CD8^+$ and $CD4^+$ T cells, stimulation of T cells to kill tumor cells, and treatment and/or prevention of cancer.

The present invention also provides functional variants of the immunogenic peptides described herein. The term "functional variant" as used herein refers to an immunogenic peptide having substantial or significant sequence identity or similarity to a parent immunogenic peptide, which functional variant retains the biological activity of the immunogenic peptide of which it is a variant. Functional variants encompass, for example, those variants of the immunogenic peptide (the parent peptide) that retain the ability to bind to an MHC Class I molecule to a similar extent, the same extent, or to a higher extent, as the parent peptide. In reference to the parent peptide, the functional variant can, for instance, be at least 30%, 50%, 75%, 80%, 90%, 98% or more identical to the parent peptide.

The functional variant can, for example, comprise the amino acid sequence of the parent immunogenic peptide with at least one conservative amino acid substitution. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Alternatively or additionally, the functional variants can comprise the amino acid sequence of the parent immunogenic peptide with at least one non-conservative amino acid substitution. In this case, it is preferable for the non-conservative amino acid substitution to not interfere with or inhibit the biological activity of the peptide. Preferably, the non-conservative amino acid substitution enhances the biological activity of the peptide.

The immunogenic peptides can consist essentially of the specified amino acid sequence, such other components of the peptide, e.g., other amino acids, do not materially change the biological, e.g., immunogenic, activity of the peptide. In this regard, the present inventive immunogenic peptide can, for example, consist essentially of the amino acid sequence SPQNSIRHNL (SEQ ID NO: 3). Also, for instance, the inventive peptide can consist essentially of the amino acid sequence of SEQ ID NO: 5.

With respect to the immunogenic peptides comprising an amino acid sequence of SEQ ID NO: 5, it is preferred that each of $X_1$, $X_2$ and $X_3$ is independently any small, aliphatic amino acid. Small aliphatic amino acids are known in the art and include, for example, Ser, Thr, or Ala. In a more preferred embodiment, $X_1$ is Ser, Thr, or Ala; $X_2$ is Thr or Ala; and $X_3$ is Ser, Thr, or Ala. In an even more preferred embodiment, the peptide comprises an amino acid sequence selected from the group consisting of: SPANSIRHNL (SEQ ID NO: 7); SPQNAIRHNL (SEQ ID NO: 8); and SPQNSARHNL (SEQ ID NO: 9).

With respect to the immunogenic peptide comprising the amino acid sequence of SEQ ID NO: 3, it is preferred that the peptide consists or consists essentially of the amino acid sequence SPQNSIRHNL (SEQ ID NO: 3). Also, with respect to the immunogenic peptides of SEQ ID NO: 3, it is preferred that the peptides are isolated and/or purified.

The immunogenic peptides of the present invention can be obtained by methods known in the art. Suitable methods of de novo synthesizing peptides are described herein and in references, such as Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwoood et al., Oxford University Press, Oxford, United Kingdom, 2000; and U.S. Pat. No. 5,449,752. Also, peptides can be recombinantly produced using the nucleic acids described herein using standard recombinant methods. See, for instance, Sambrook et al., *Molecular Cloning: A Laboratory Manual*, $3^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994. Further, some of the immunogenic peptide can be isolated and/or purified from a source, such as a plant, a bacterium, a mammal, e.g., a rat, a human, etc. Methods of isolation and purification are well-known in the art. Alternatively, the peptides described herein can be commercially synthesized by companies, such as Synpep (Dublin, Calif.), Peptide Technologies Corp. (Gaithersburg, Md.), and Multiple Peptide Systems (San Diego, Calif.). In this respect, the immunogenic peptides of the present invention can be synthetic, recombinant, isolated, and/or purified.

The present invention further provides a fusion protein comprising at least one of the immunogenic peptides (including functional portions and variants thereof) described herein and an MHC Class I molecule, or a portion thereof. The MHC Class I molecule can be any of the MHC Class I molecules known in the art, such as any of those described herein. Preferably, the MHC Class I molecule is HLA-B7. The portion of the MHC Class I molecule can be any part of the MHC Class I molecule. Preferably, the portion comprises the peptide binding portion of the MHC Class I molecule. More preferably, the portion comprises the peptide binding portion and the T cell receptor binding portion of the MHC Class I molecule. Such portions of MHC Class I molecules are known in the art.

The fusion protein can comprise one or more copies of the immunogenic peptide and/or one or more copies of the MHC Class I molecule or part thereof. For instance, the fusion protein can comprise 1, 2, 3, 4, 5, or more copies of the immunogenic peptide and/or of the MHC Class I molecule or part thereof. Suitable methods of making fusion proteins are known in the art, and include, for example, recombinant methods. See, for instance, Choi et al., *Mol Biotechnol* 31: 193-202 (2005).

The present invention further provides conjugates, e.g., bioconjugates, comprising any of the immunogenic peptides (including any of the functional portions or variants thereof). Conjugates, as well as methods of synthesizing conjugates of peptides in general, are known in the art (See, for instance, Hudecz, F., *Methods Mol Biol* 298: 209-223 (2005) and Kirin et al., *Inorg Chem* 44(15): 5405-5415 (2005)).

The present invention provides a nucleic acid comprising a nucleotide sequence encoding any of the immunogenic peptides, functional portions or variants thereof, or fusion proteins thereof, described herein. By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the present invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-$N^2$-carboxypropyl) uracil, (acp3) w, and 2,6-diaminopurine. Alternatively, one or more of the nucleic acids of the present invention can be purchased from companies, such as Macromolecular Resources (Fort Collins, Colo.) and Synthegen (Houston, Tex.).

The nucleic acids of the present invention can be incorporated into an expression vector. In this regard, the present invention provides expression vectors comprising any of the nucleic acids of the present invention. For purposes herein, the term "expression vector" means a genetically-modified oligonucleotide (i.e., polynucleotide) construct that permits the expression of a protein or a peptide by a host cell, when the construct comprises a nucleotide sequence encoding the protein or peptide, and the vector is contacted with the cell under conditions sufficient to have the protein expressed within the cell. The vectors of the present invention are not naturally-occurring as a whole. However, parts of the vectors can be naturally-occurring. The present inventive expression vectors can comprise any type of nucleotides, including, but not limited to DNA and RNA, which can be single-stranded or double-stranded, synthesized or obtained in part from natural sources, and which can contain natural, non-natural or altered nucleotides. The expression vectors can comprise naturally-occurring, non-naturally-occurring internucleotide linkages, or both types of linkages. Preferably, the non-naturally occurring or altered nucleotides or internucleotide linkages does not hinder in any way the transcription or replication of the vector.

The expression vector of the present invention can be any suitable expression vector, and can be used to transform or transfect any suitable host. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-C1, pMAM and pMAMneo (Clontech).

The expression vectors of the present invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papilloma virus, and the like.

Desirably, the expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the present inventive expression vectors include, for instance, neomycin/G418 resistance genes, hygromycin resistance genes, histidinol resistance genes, tetracycline resistance genes, and ampicillin resistance genes.

The expression vector can comprise a native or normative promoter operably linked to the nucleic acid encoding the protein. The selection of promoters, e.g., strong, weak, inducible, tissue-specific and developmental-specific, is within the ordinary skill of the artisan. Similarly, the combining of a nucleic acid with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The present inventive expression vectors can be designed for either transient expression, for stable expression, or for both. Also, the expression vectors can be made for constitutive expression or for inducible expression. Further, the expression vectors can be made to include a suicide gene.

As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, *Suicide Gene Therapy: Methods and Reviews*, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

The present invention further provides a host cell comprising any of the expression vectors described herein. As used herein, the term "host cell" refers to any type of cell that can contain the present inventive expression vector. The host cell can be a eukaryotic cell, e.g., plant, animal, fungi, or algae, or can be a prokaryotic cell, e.g., bacteria or protozoa. The cell can be a cultured cell or a primary cell, i.e., isolated directly from an organism, e.g., a human. The cell can be an adherent cell or a suspended cell, i.e., a cell that grows ill suspension. Suitable host cells are known in the art and include, for instance, DH5α *E. coli* cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5α cell. For purposes of producing a recombinant protein, the host cell is preferably a mammalian cell. Most preferably, the host cell is a human cell. While the host cell can be of any cell type, can originate from any type of tissue, and can be of any developmental stage, the host cell preferably is an antigen presenting cell, such as, for instance, a dendritic cell, a macrophage, or a B cell. Preferably, the host cell is a dendritic cell.

The present invention further provides an antibody, or an antigen binding portion thereof, that binds to any of the immunogenic peptides described herein. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for the peptide of the present invention. Desirably, the antibody is specific for the peptide, such that there is minimal cross-reaction with other peptides or proteins.

Methods of testing antibodies for the ability to bind to any of the immunogenic peptides are known in the art an include any antibody-antigen binding assay, such as, for example, radioimmunoassay (RIA), ELISA, Western blot, immunoprecipitation, and competitive inhibition assays (see, e.g., Janeway et al., supra, and U.S. Patent Application Publication No. 2002/0197266 A1).

Suitable methods of making antibodies are known in the art. For instance, standard hybridoma methods are described in, e.g., Köhler and Milstein, *Eur. J. Immunol.*, 5, 511-519 (1976), Harlow and Lane (eds.), *Antibodies: A Laboratory Manual*, CSH Press (1988), and C. A. Janeway et al. (eds.), *Immunobiology*, 5th Ed., Garland Publishing, New York, N.Y. (2001)). Alternatively, other methods, such as EBV-hybridoma methods (Haskard and Archer, *J. Immunol. Methods*, 74(2), 361-67 (1984), and Roder et al., *Methods Enzymol.*, 121, 140-67 (1986)), and bacteriophage vector expression systems (see, e.g., Huse et al., *Science*, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1).

Phage display furthermore can be used to generate the antibody of the present invention. In this regard, phage libraries encoding antigen-binding variable (V) domains of antibodies can be generated using standard molecular biology and recombinant DNA techniques (see, e.g., Sambrook et al. (eds.), *Molecular Cloning, A Laboratory Manual*, 3rd Edition, Cold Spring Harbor Laboratory Press, New York (2001)). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., *J. Mol. Biol.*, 235, 959-973 (1994).

The present inventive invention also provides antigen binding portions of any of the antibodies described herein. The antigen binding portion can be any portion that has at least one antigen binding site, such as Fab, F(ab')$_2$, dsFv, sFv, diabodies, and triabodies.

A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., *Protein Engineering*, 7, 697-704 (1994)). Antibody fragments of the present invention, however, are not limited to these exemplary types of antibody fragments.

The present inventive immunogenic peptides, fusion proteins, conjugates, nucleic acids, expression vectors, host cells, and antibodies, can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least 50%, can be greater than 60%, 70% or 80%, or can be 100%.

The present inventive immunogenic peptides (including functional portions and variants thereof), fusion proteins, conjugates, nucleic acids, expression vectors, host cells, and antibodies (including antigen binding portions thereof), all of which are collectively referred to as "immunogenic materials" hereinafter, can be formulated into a composition, such as a pharmaceutical composition. In this regard, the present invention provides a pharmaceutical composition comprising any of the immunogenic peptides, fusion proteins, conjugates, nucleic acids, expression vectors, host cells, and antibodies, and a pharmaceutically acceptable carrier. The present inventive pharmaceutical compositions containing any of the immunogenic materials can comprise more than one immunogenic material, e.g., a peptide and a nucleic acid, or two or more different peptides. Alternatively, the pharmaceutical composition can comprise an immunogenic material in combination with another pharmaceutically active agents or drugs, such as a chemotherapeutic agents e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used and is limited only by chemico-physical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular immunogenic material, as well as by the particular method used to administer the immunogenic material. Accordingly, there are a variety of suitable formulations of the pharmaceutical composition of the present invention. The following formulations for oral, aerosol, parenteral, subcutaneous, intravenous, intramuscular, intraarterial, intrathecal, interperitoneal, rectal, and vaginal administration are exemplary and are in no way limiting. More than one route can be used to administer the immunogenic materials, and in certain instances, a particular route can provide a more immediate and more effective response than another route.

Topical formulations are well-known to those of skill in the art. Such formulations are particularly suitable in the context of the present invention for application to the skin.

Formulations suitable for oral administration can consist of (a) liquid solutions, such as an effective amount of the immunogenic material dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the immunogenic material in a flavor, usually sucrose and acacia or tragacanth, as well as pastilles comprising the immunogenic material in an inert base, such as gelatin and glycerin, or sucrose and acacia, emulsions, gels, and the like containing, in addition to, such excipients as are known in the art.

The immunogenic material, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The immunogenic material can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1,3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the immunogenic material in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Injectable formulations are in accordance with the present invention. The requirements for effective pharmaceutical carriers for injectable compositions are well-known to those of ordinary skill in the art (see, e.g., *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Toissel, 4th ed., pages 622-630 (1986)). Preferably, when administering cells, e.g., dendritic cells, the cells are administered via injection.

Additionally, the immunogenic materials, or compositions comprising such immunogenic materials, can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

It will be appreciated by one of skill in the art that, in addition to the above-described pharmaceutical compositions, the immunogenic materials of the present invention can be formulated as inclusion complexes, such as cyclodextrin inclusion complexes, or liposomes.

For purposes of the present invention, the amount or dose of the immunogenic material administered should be sufficient to effect, e.g., a therapeutic or prophylactic response, in the subject or animal over a reasonable time frame. For example, the dose of the immunogenic material should be sufficient to bind to an MHC Class I molecule, stimulate tumor cell killing, stimulate $CD4^+$ and $CD8^+$ T cells, or treat or prevent cancer in a period of from about 2 hours or longer, e.g., 12 to 24 or more hours, from the time of administration. In certain embodiments, the time period could be even longer. The dose will be determined by the efficacy of the particular immunogenic material and the condition of the animal (e.g., human), as well as the body weight of the animal (e.g., human) to be treated.

Many assays for determining an administered dose are known in the art. For purposes of the present invention, an assay, which comprises comparing the extent to which $CD8^+$ T cells are stimulated to kill tumor cells upon administration of a given dose of a immunogenic material to a mammal among a set of mammals of which is each given a different dose of the immunogenic material, could be used to determine a starting dose to be administered to a mammal. The extent to which the tumor cells are killed upon administration of a certain dose can be assayed by methods known in the art, including, for instance, the method described herein as Example 3.

The dose of the immunogenic material also will be determined by the existence, nature and extent of any adverse side effects that might accompany the administration of a particular immunogenic material. Typically, the attending physician will decide the dosage of the immunogenic material with which to treat each individual patient, taking into consideration a variety of factors, such as age, body weight, general health, diet, sex, immunogenic material to be administered, route of administration, and the severity of the condition being treated. By way of example and not intending to limit the present invention, the dose of the immunogenic material can be about 0.001 to about 1000 mg/kg body weight of the subject being treated/day, from about 0.01 to about 10 mg/kg body weight/day, about 0.01 mg to about 1 mg/kg body weight/day.

One of ordinary skill in the art will readily appreciate that the immunogenic materials of the present invention can be modified in any number of ways, such that the therapeutic or prophylactic efficacy of the immunogenic materials is increased through the modification. For instance, the immunogenic materials can be conjugated either directly or indirectly through a linker to a targeting moiety. The practice of conjugating compounds, e.g., immunogenic materials, to targeting moieties is known in the art. See, for instance, Wadwa et al., *J. Drug Targeting* 3: 111 (1995) and U.S. Pat. No. 5,087,616. The term "targeting moiety" as used herein, refers to any molecule or agent that specifically recognizes and binds to a cell-surface receptor, such that the targeting moiety directs the delivery of the immunogenic materials to a population of cells on which surface the receptor is expressed. Targeting moieties include, but are riot limited to, antibodies, or fragments thereof, peptides, hormones, growth factors, cytokines, and any other natural or non-natural ligands, which bind to cell surface receptors (e.g., Epithelial Growth Factor Receptor (EGFR), T-cell receptor (TCR), B-cell receptor (BCR), CD28, Platelet-derived Growth Factor Receptor (PDGF), nicotinic acetylcholine receptor (nAChR), etc.). The term "linker" as used herein, refers to any agent or molecule that bridges the immunogenic materials to the targeting moiety. One of ordinary skill in the art recognizes that sites on the immunogenic materials, which are not necessary for the function of the immunogenic materials, are ideal sites for attaching a linker and/or a targeting moiety, provided that the linker and/or targeting moiety, once attached to the immunogenic materials, do(es) not interfere with the function of the immunogenic materials, i.e., the ability to bind to an MHC Class I molecule, to stimulate $CD4^+$ and $CD8^+$ T cells, to stimulate the killing of tumor cells, or to treat or prevent cancer.

Alternatively, the immunogenic materials can be modified into a depot form, such that the manner in which the immunogenic materials is released into the body to which it is administered is controlled with respect to time and location within the body (see, for example, U.S. Pat. No. 4,450,150). Depot forms of immunogenic materials can be, for example, an implantable composition comprising the immunogenic materials and a porous or non-porous material, such as a polymer, wherein the immunogenic materials is encapsulated by or diffused throughout the material and/or degradation of the non-porous material. The depot is then implanted into the desired location within the body and the immunogenic materials are released from the implant at a predetermined rate.

The present inventive immunogenic peptides (including functional portions and variants thereof), fusion proteins, conjugates, nucleic acids, expression vectors, and host cells can be made as part of a vaccine. As such, the present invention also provides a vaccine comprising any of the immunogenic peptides, fusion proteins, nucleic acids, expression vectors, and host cells described herein. The term "vaccine" as used herein means any substance that causes activation of an animal's immune system without causing actual disease. The vaccines of the present invention comprise an immunogen that induces an immune response directed against a tumor antigen, e.g., PAX3-FKHR. The immunogen of the present inventive vaccines is any of the immunogenic peptides, fusion proteins, nucleic acids, expression vectors, and host cells described herein.

In one embodiment, the vaccine is an expression vector encoding a PAX3-FKHR peptide. To provide a vaccine to an individual, a nucleotide sequence which encodes for the PAX3-FKHR peptide is inserted into a expression vector, as described above, and introduced into the mammal to be immunized. Examples of vectors that may be used in the aforementioned vaccines include, but are not limited to, defective retroviral vectors, adenoviral vectors vaccinia viral vectors, fowl pox viral vectors, or other viral vectors (Mulligan, R. C., (1993) Science 260:926-932). The viral vectors carrying the PAX3-FKHR nucleic acid can be introduced into a mammal either prior to any evidence of the disease, e.g., cancer, or to mediate regression of the disease in a mammal afflicted with the disease. Examples of methods for administering the viral vector into the mammals include, but are not limited to, exposure of cells to the virus ex vivo, or injection of the retrovirus or a producer cell line of the virus into the affected tissue or intravenous administration of the virus. Alternatively, the viral vector carrying all or part of the PAX3-FKHR nucleic acid sequence may be administered locally by direct injection or topical application in a pharmaceutically acceptable carrier.

The quantity of viral vector carrying the PAX3-FKHR nucleic acid sequence to be administered is based on the titer of virus particles. A preferred range of the immunogen to be administered may be about $10^6$ to about $10^{11}$ virus particles per mammal, preferably a human. After immunization, the efficacy of the vaccine can be assessed by production of antibodies or immune cells that recognize the antigen (PAX3-FKHR), as assessed by specific lytic activity or specific cytokine production or by regression of the disease. One skilled in the art knows the conventional methods to assess the aforementioned parameters. If the mammal to be immunized is already afflicted with the disease, the vaccine can be administered in conjunction with other therapeutic treatments. Examples of other therapeutic treatments includes, but are not limited to, adoptive T cell immunotherapy, coadministration of cytokines or other therapeutic drugs for the disease.

Alternatively, the PAX3-FKHR peptides may be administered as a vaccine in a pharmaceutically acceptable carrier. Ranges of PAX3-FKHR peptide that may be administered are about 0.001 to about 100 mg per patient, preferred doses are about 0.01 to about 100 mg per patient. Immunization is repeated as necessary, until a sufficient titer of anti-immunogen antibody or immune cells has been obtained.

In yet another alternative embodiment, mammalian cells expressing the PAX3-FKHR antigen can be administered to mammals and serve as a vaccine. Examples of mammalian cells include, but are not limited to, primary manmalian cultures or continuous mammalian cultures, COS cells, NIH3T3, or 293 cells (ATCC #CRL 1573). Examples of how the cells expressing PAX3-FKHR antigens can be administered include, but not limited to, intravenous, intraperitoneal or intralesional administration.

In yet another embodiment of this invention, PAX3-FKHR peptides, may be exposed to dendritic cells cultured in vitro. The cultured dendritic cells provide a means of producing T-cell dependent antigens comprised of dendritic cell modified antigen or dendritic cells pulsed with antigen, in which the antigen is processed and expressed on the antigen activated dendritic cell. The PAX3-FKHR antigen-activated dendritic cells or processed dendritic cell antigens may be used as immunogens for vaccines or for the treatment of cancer. The dendritic cells should be exposed to antigen for sufficient time to allow the antigens to be internalized and presented on the dendritic cells surface. The resulting dendritic cells or the dendritic cell process antigens can than be administered to an individual in need of therapy. Such methods are described in Steinman et al. (WO 93/208185) and in Banchereau et al. (EP Application 0563485A1) which are incorporated herein by reference.

Vaccination can be conducted by conventional methods. For example, the immunogen can be used in a suitable diluent, such as saline or water, or a complete or incomplete adjuvant. Further, the immunogen can be bound or unbound to a carrier to make the peptide immunogenic. Examples of such carrier molecules include but are not limited to bovine serum albumin (BSA), keyhole limpet hemocyanin (KLH), tetanus toxoid, and the like. The immunogen also can be coupled with a lipoprotein or administered in liposomal form or with adjuvants. The immunogen can be administered by any route appropriate for antibody production such as intravenous, intraperitoneal, intramuscular, subcutaneous, and the like. The immunogen may be administered once or at periodic intervals until a significant titer of anti-PAX3-FKHR immune cells or anti-PAX3-FKHR antibody is produced. The presence of anti-PAX3-FKHR immune cells may be assessed by measuring the frequency of precursor CTL against PAX3-FKHR antigen prior to and after immunization by a CTL precursor analysis assay (Coulie, P. et al., (1992) *Internat J Can* 50:289-297). The antibody may be detected in the serum using standard immunoassays known in the art.

The vaccine formulations may be evaluated first in animal models, initially rodents, and in non-human primates and finally in humans. The safety of the immunization procedures is determined by looking for the effect of immunization on the general health of the immunized animal (weight change, fever, appetite behavior etc.) and looking for pathological changes on autopsies. After initial testing in animals, diseased patients can be tested. Conventional methods would be used to evaluate the immune response of the patient to determine the efficiency of the vaccine.

The vaccine may be used either prophylactically or therapeutically. When provided prophylactically, the vaccine is provided in advance of any evidence of disease, e.g., cancer. The prophylactic administration of the vaccine should serve to prevent or attenuate the disease in a mammal. In a preferred embodiment, mammals, preferably humans, at high risk for the disease are prophylactically treated with the vaccines of the present invention. Examples of such mammals include, but are not limited to, humans with a family history of the disease or humans previously afflicted with the disease and therefore at risk for re-occurrence. When provided therapeutically, the vaccine is provided to enhance the patient's own immune response to the antigen, e.g., tumor antigen, present in the patient.

It is contemplated that the present inventive pharmaceutical compositions and vaccines can be used in methods of treating or preventing cancer. Without being bound to any particular theory, it is believed that the present inventive peptides bind to a MHC Class I molecule, e.g., HLA-B7, and to a T cell receptor, such that the corresponding T cell is stimulated to create an immune response, e.g., a cellular immune response. More particularly, the T cells having the TCR, which binds to the peptides of the present invention, once bound to the peptide are stimulated to lyse and/or kill the target cell, e.g., a tumor cell. In this respect, the present invention provides a method of stimulating a T cell to kill a tumor cell. The method comprises contacting a T cell with a cell presenting on its surface any of the immunogenic peptides described herein and with a tumor cell in a manner effective for the T cell to kill the tumor cell.

The tumor cell lysed by the T cell can be any type of tumor cell, such as, for instance, a tumor cell from a benign tumor or a cancerous tumor. The tumor cell can be a tumor cell from any of the following cancers: alveolar rhabdomyosarcoma, breast cancer, prostate cancer, lung cancer, colon cancer, rectal cancer, urinary bladder cancer, non-Hodgkin lymphoma, melanoma, renal cancer, pancreatic cancer, cancer of the oral cavity, pharynx cancer, ovarian cancer, thyroid cancer, stomach cancer, brain cancer, multiple myeloma, esophageal cancer, liver cancer, cervical cancer, larynx cancer, cancer of the intrahepatic bile duct, acute myeloid leukemia, soft tissue cancer, small intestine cancer, testicular cancer, chronic lymphocytic leukemia, Hodgkin lymphoma, chronic myeloid cancer, acute lymphocytic cancer, cancer of the anus, anal canal, or anorectum, cancer of the vulva, cancer of the neck, gallbladder, or pleura, malignant mesothelioma, bone cancer, cancer of the joints, hypopharynx cancer, cancer of the eye, cancer of the nose, nasal cavity, or middle ear, nasopharynx cancer, ureter cancer, peritoneum, omentum, and mesentery cancer, or gastrointestinal carcinoid tumor. Preferably, the tumor cell is an alveolar rhabdomyosarcoma cell.

With respect to the present inventive method of stimulating a T cell to kill a tumor cell, the T cell can be contacted with the tumor cell and the peptide-presenting cell simultaneously or sequentially. For instance, the T cell can be contacted with the peptide-presenting cell before being contacted with the tumor cell. Alternatively, the T cell can be contacted with the tumor cell and the peptide-presenting cell at the same time.

Also, the T cell can be contacted with the peptide-presenting cell in vitro, in vivo or ex vivo. For example, the T cell can be contacted with the peptide-presenting cell in vitro or ex vivo and then subsequently contacted with the tumor cell in vivo. Alternatively, the T cell can be contacted with the peptide-presenting cell in vivo and then subsequently contacted with the tumor cell in vivo, or can be contacted with the peptide-presenting cell and the tumor cell in vivo and simultaneously.

In a preferred embodiment, the method provides for the killing of multiple tumor cells in a manner effective to treat cancer in a mammal. In this regard, the present invention provides a method of treating cancer. Preferably, the T cells are autologous to the mammal being treated.

Further, without being bound to any particular theory, some of the present inventive peptides can also be able to stimulate $CD4^+$ T cells, such that the T cells help B cells to produce antibodies against the peptides. In this regard, the peptides desirably stimulate a humoral immune response, in addition to the cellular immune response mediated through the $CD8^+$ T cells. Accordingly, the present invention also provides methods of stimulating $CD4^+$ and $CD8^+$ T cells. The method comprises contacting a $CD4^+$ and a $CD8^+$ T cell with any of the dendritic cells described herein.

With respect to the present inventive method of stimulating a $CD4^+$ T cell and a $CD8^+$ T cell, the T cell can be contacted with the $CD4^+$ T cell and a $CD8^+$ T cell simultaneously or sequentially. For instance, the $CD4^+$ T cell can be contacted with the dendritic cell at the same or different time as the time that the $CD8^+$ T cell is contacted with the dendritic cell.

Also, either of the $CD4^+$ T cell and the $CD8^+$ T cell can be contacted with the dendritic cell in vitro, in vivo or ex vivo. For example, the $CD8^+$ T cell can be contacted with the dendritic cell in vitro or ex vivo. Alternatively, the T cell can be contacted with the dendritic cell in vivo.

In a preferred embodiment, the T cells, e.g., the $CD8^+$ T cells, are contacted with a tumor cell after being contacted with the dendritic cell, such that the T cell lyses and kills the tumor cell.

In a more preferred embodiment, the method provides for the killing of multiple tumor cells in a manner effective to treat cancer in a mammal. In this regard, the present invention provides a method of treating cancer. Preferably, the T cells are autologous to the mammal being treated.

A method of treating or preventing cancer in a mammal is further provided herein. The method comprises administering to the mammal any of the pharmaceutical compositions or vaccines described herein in an amount effective to treat or prevent cancer in the mammal.

With respect to the methods of treating or preventing cancer, the cancer can be any cancer, such as any of those described herein. Preferably, the cancer is alveolar rhabdomyosarcoma.

With respect to the methods of treating or preventing cancer, the pharmaceutical compositions or vaccines can be administered by any method known in the art, including any of the routes described herein. As one of ordinary skill in the art recognizes, some pharmaceutical compositions and vaccines are more amenable to certain routes than others. For example, it is preferable for the pharmaceutical compositions and vaccines comprising host cells to be administered through injection, as opposed to orally or transdermally. The route appropriate for the particular pharmaceutical composition or vaccine can easily be determined by one of ordinary skill in the art.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the present inventive methods can provide any amount of any level of treatment or prevention of cancer in a mammal.

As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The following examples further illustrate the invention but, of course, should not be construed as in any way limiting its scope.

EXAMPLES

The following cell lines and peptides are used in the examples described herein below.

C1R.B7, a specific transfectant of the B lymphoblastoid C1R cell line, which, in native form, expresses no endogenous HLA-A or HLA-B gene products (Storkus et al., *Proc. Natl. Acad. Sci.,* 86, 2361-2364 (1999)), is a gift of William Biddison (National Institute of Neurological Disorders and Stroke, NIH, Bethesda, Md.). T2.B7 is a specific transfectant of the hybrid B and T lymphoblastoid T2 cell line, which is deficient in TAP1 and TAP2 gene expression (Salter et al., *Immunogenetics* 21: 235-246 (1985); and Spies and DeMars, *Nature* 351: 323-324 (1991)), and which is a gift of Peter Cresswell (Yale University, New Haven, Conn.). The Rh5 alveolar rhabdomyosarcoma cell line is kindly provided by Dr. P. Houghton (St Jude's Children's Research Hospital). The RD and CTR embryonal rhabdomyosarcoma cell lines are obtained from the American Type Culture Collection and Dr. M. Tsokos (National Cancer Institute), respectively. Cell lines are maintained in culture medium with heat inactivated fetal calf serum (FCS) (10% v/v). Culture medium consists of RPMI1640 medium (Cellgro, Bethesda, Md.) containing L-glutamine (2 mM), penicillin (100 IU/ml), streptomycin (100 µg/ml), nonessential amino acids (10 µl/ml), sodium-pyruvate (1.0 mM), gentamicm (25 µg/ml), and 2-mercapto-ethanol (50 µM).

Full-length peptides are purchased from Peptide Technologies Corp. (Gaithersburg, Md.) and from Multiple Peptide Systems (San Diego, Calif.) at >95% purity and are single peaks by reverse-phase high-performance liquid chromatography. Optimal epitopes are synthesized on an automated peptide synthesizer (Symphony Multiplex; Protein Technologies, Phoenix, Ariz.) using 9-fluoroenylmethyloxycarbonyl chemistry (Stewart et al., *Solid Phase Peptide Synthesis,* $2^{nd}$ ed., Rockford, Ill., Pierce Chemical Company, 1984). The peptides are cleaved from the resin with trifluoroacetic acid. Purification to single peaks is achieved using reverse-phase high-performance liquid chromatography on bondapack reverse-phase CIS columns (Waters Associates, Milford, Mass.).

Example 1

This example demonstrates the binding of a PAX3-FKHR peptide epitope to a MHC Class I molecule.

A chromosomal translocation-generated fusion protein breakpoint peptide, RS10 (SPQNSIRHNL), is selected on the basis of predicted potential binding to HLA-B7 (Rammensee et al., *Immunogenetics* 41: 178-228 (1995)). Peptide binding to HLA-B7 is assessed by using stabilization of HLA-B7 molecules on the surface of T2-B7 cells that lack the TAP transporter and therefore express only short-lived empty HLA-B7 molecules unless a peptide is present that can bind and stabilize them. These assays are described in (Stuber et al., *Eur. J. Immunol.,* 22, 2697-2703 (1992), Nijman et al., *Eur. J. Immunol.,* 23, 1215-1219 (1993), Zeh et al., *Hum. Immunol.,* 39, 79-86 (1994), and Smith et al., *Internat. Immunol.,* 9, 1085-1093 (1997)). Cells of the TAP1/TAP2-deficient T2 cell line (Salter et al., *Immunogenetics,* 21, 235-246 (1985), and Spies et al., *Nature,* 351, 323-324 (1991)) transfected with the HLA-B7 gene are suspended in culture medium containing heat inactivated FCS (2.5% v/v) and added to 96-well round-bottomed plates at $2\times10^5$ cells/well. Human β2-microglobulin (Sigma Chemical Co.) is also added at 20 µg/well. Where appropriate, peptide is added to the desired concentration. The cells are then incubated overnight at 37° C. in 5% $CO_2$, followed by washing with PBS containing $NaN_3$ (0.5% w/v and FCS 2% v/v). Next, cells are incubated on ice for 30 min in the presence of primary anti-HLA-B7 specific antibody (BB7.1 hybridoma culture supernatant; ATCC), followed by washing and incubation for 30 min in goat anti-mouse immunoglobulin FITC (Becton Dickinson). Analysis is performed by flow cytometry.

Conventional mAb staining is conducted in PBS containing 0.01% sodium azide on ice. Cells are labeled with FITC- or PE-conjugated nAbs obtained from BD PharMingen (San Diego, Calif.). For each staining of interest, the appropriate isotype-matched control is included. All reagents are used at optimal concentration as determined experimentally. Flow cytometric analysis is performed with a FACScan (BD Biosciences, Mountain View, Calif.). Data are collected on 5000-10,000 viable cell events and analyzed with CellQuest software.

Based on these binding assays, the RS10 peptide is found to bind HLA-B7 in a binding assay (data not shown).

This example demonstrated that the RS10 peptide binds to an MHC Class I molecule.

Example 2

This example demonstrates a method of making dendritic cells pulsed with the present inventive peptides and T cells specific for the peptides of the present invention.

To determine whether this peptide could elicit human CTL, dendritic cells presenting the RS10 peptide are generated. Specifically, leukopheresed human mononuclear cells are elutriated from an HLA-B7$^+$ normal healthy blood donor to separate a monocyte and a lymphocyte fraction. The monocyte fraction is converted into dendritic cells by growth in GM-CSF and IL-4 and maturation with CD40L. Specifically, elutriated monocytes and lymphocytes are obtained from apheresed HLA-B7-positive subjects from the NIH normal donor pool. Monocytes are cultured for 7 days in 75 cm$^2$ culture flasks (Costar Corporation) at 3.5×10$^6$ cells/ml in culture medium containing heat inactivated autologous plasma (10% v/v), h-IL-4 (800 U/ml; R&D) and h-GMCSF (50 ng/ml; Immunex) at 37° C. in an atmosphere of 5% CO$_2$ in air. At day 3, the cells are re-fed by removing 5 ml of the medium from the culture flasks and adding back 5 ml of fresh culture medium supplemented with cytokines (h-IL4: 400 U/ml; h-GMCSF: 25 ng/ml). At day 4, CD40 ligand trimer (Immunex Corp., now Amgen, Seattle) is added at 1 μg/ml (Cella et al., *J. Exp. Med.*, 184, 747-752, (1996)). Cells are harvested on day 6 and stained for CD14, CD19, CD56, CD80, CD83, CD86, and HLA-DR antigens. The staining is then quantified by flow cytometry as described above.

The DCs are found to be strongly positive for CD80 and CD86 costimulatory molecules, HLA-DR, and the maturation marker CD83, but are negative for CD14, CD19, and CD56 (data not shown).

The DCs are then pulsed with the RS10 peptide and used to stimulate autologous lymphocytes from the same apheresis to generate a specific CTL line. Specifically, lymphocytes are suspended in culture medium containing heat inactivated autologous plasma (10% v/v)) and plated in a 24-well plate at 4×10$^6$ cells/well. Autologous dendritic cells are pulsed with RS10 peptide (10 μM) in culture medium for 4 hours. Next, the dendritic cells are irradiated with 3000 rads and added to the lymphocytes at 4×10$^5$ cells/well. The next day (day 1), cultures are supplemented with hIL-2 (12.5 U/ml), hIL-7 (2400 U/ml), hIL-1β (150 U/ml) and hIL-12 (±1 ng/ml). At day 7, the cells are harvested, washed, plated in a 24-well plate at 1.5×10$^6$ cells/well, and restimulated with irradiated RS10 pulsed autologous DCs (1.5×10$^5$ cells/well). At day 8, the cells are supplemented with IL-2 (12.5 U/ml) and hIL-7 (2400 U/ml). Restimulations are done weekly using the same conditions. Cultures are checked every week for relative CD4, CD8, and CD56 expression and, if necessary, depleted of CD4$^+$ or CD56+ cells by magnetic cell sorting using Magnetic Micro Beads (Miltenyi Biotec Midi-MACS).

The line is found to express CD8, but not CD4 and CD56 (data not shown).

This example demonstrated the generation and characterization of DCs pulsed with PAX3-FKHR peptide and the generation and characterization of a CTL line specific for the PAX3-FKHR peptide and MHC molecule expressed on the DCs.

Example 3

This example demonstrates that the peptides of the present invention stimulate T cells to kill tumor cells.

The human CTL line generated and characterized in Example 2 is tested for the ability to kill human C1R-B7 target cells pulsed with the specific RS10 peptide or a control SSI peptide from synovial sarcoma that also binds HLA-B7 (Worley et al., *Cancer Res.*, 61, 6868-6875 (2001)) (FIG. 1). In particular, specific cytotoxic activities are determined in a standard 4 h $^{51}$Cr release assay at various effector:target (E:T) ratios. Briefly, graded doses of viable effector cells are plated in triplicate in 96-well U-bottom culture plates (Corning Glass, Corning, N.Y.) and co-cultured for 4 h with sodium chromate-labeled (100 μCi; NEN, Boston, Mass.) peptide pulsed (10 μM) C1R-B7 target cells. In some experiments, the Rh5, RD and CTR tumor cell lines are used as a target. Supernatants are collected, radioactivity measured, and specific lysis is calculated according to the equation: percentage of specific cytotoxicity=(experimental cpm−spontaneous cpm)/(maximum cpm−spontaneous cpm)×100.

Maximum $^{51}$Cr release is determined from supernatants of lysed target cells incubated with Triton X-100 (5% v/v). Spontaneous release is determined from target cells incubated without added effector cells.

Figure 2:
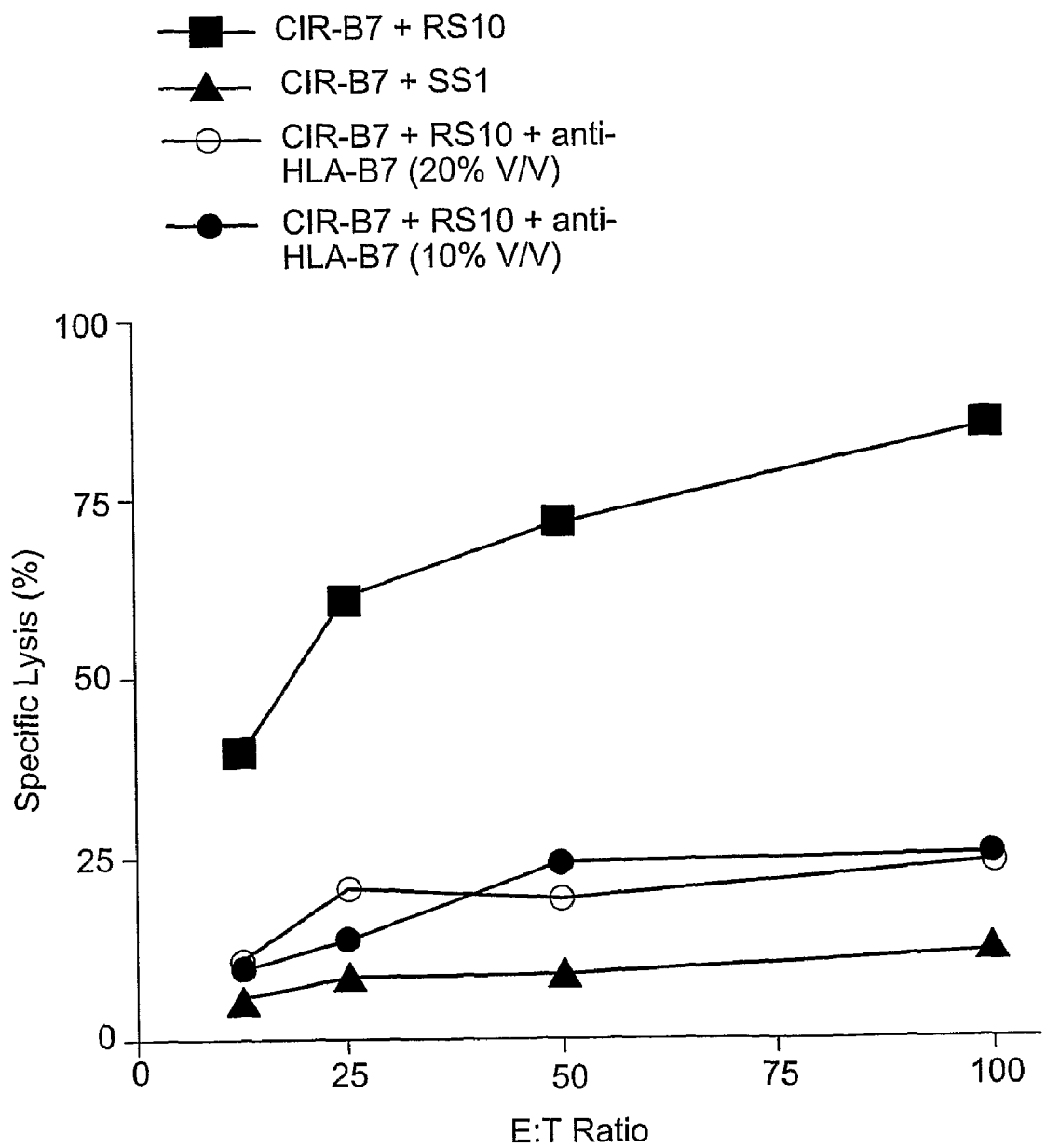

The lysis is clearly specific for the PAX-FKHR-derived RS10 peptide. Furthermore, the killing is restricted by the human HLA-B7 class I MHC molecule as demonstrated by blockade of killing with antibody to HLA-B7 (FIG. 2).

This example demonstrated that the generated CTL can lyse tumor cells.

Example 4

This example demonstrates that human CTL specific for the RS10 PAX-FKHR fusion peptide kill rhabdomyosarcoma cells expressing HLA-B7.

Figure 3:
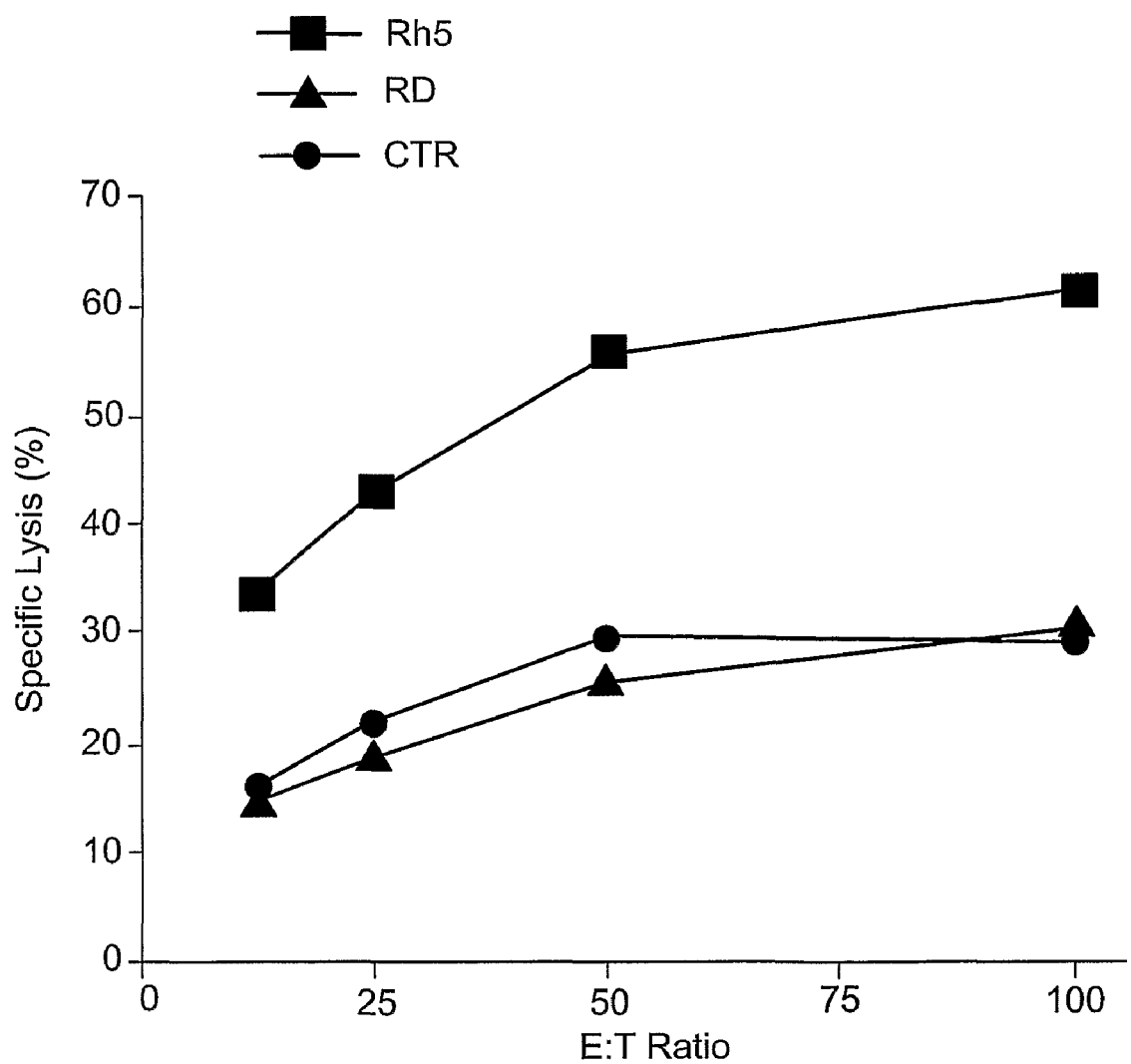
FIG. 3 depicts the CTL lytic activity at different E:T ratios. The effector cells are the CTL generated in Example 2 described herein, while the target cells are rhabdomyosarcoma cells expressing HLA-B7 (Rh5; squares), or two control cell lines, RD (triangles) or CTR (circles), which do not express HLA-B7.

To determine whether this RS10 epitope is naturally processed and presented by HLA-B7 in human tumor cells that express endogenous PAX-FKHR fusion protein, the lytic ability of the RS10-specific CTL line is tested against a rhabdomyosarcoma tumor cell expressing HLA-B7 (Rh5), and two control lines RD and CTR not expressing HLA-B7 (FIG. 3). CTL activity is assessed as described in Example 3.

Clear specific lysis of the Kh5 cells compared to the other control tumor cells indicates 1) that the RS10 epitope is indeed naturally endogenously processed and presented in unmanipulated human tumor cells, and 2) that CTL raised against this epitope could kill human tumor cells.

This example demonstrated that human CTL specific for the RS10 peptide kill tumor cells expressing an MHC Class I molecule.

Example 5

This example demonstrates the generation and testing of variant peptides of RS10.

Figure 4:
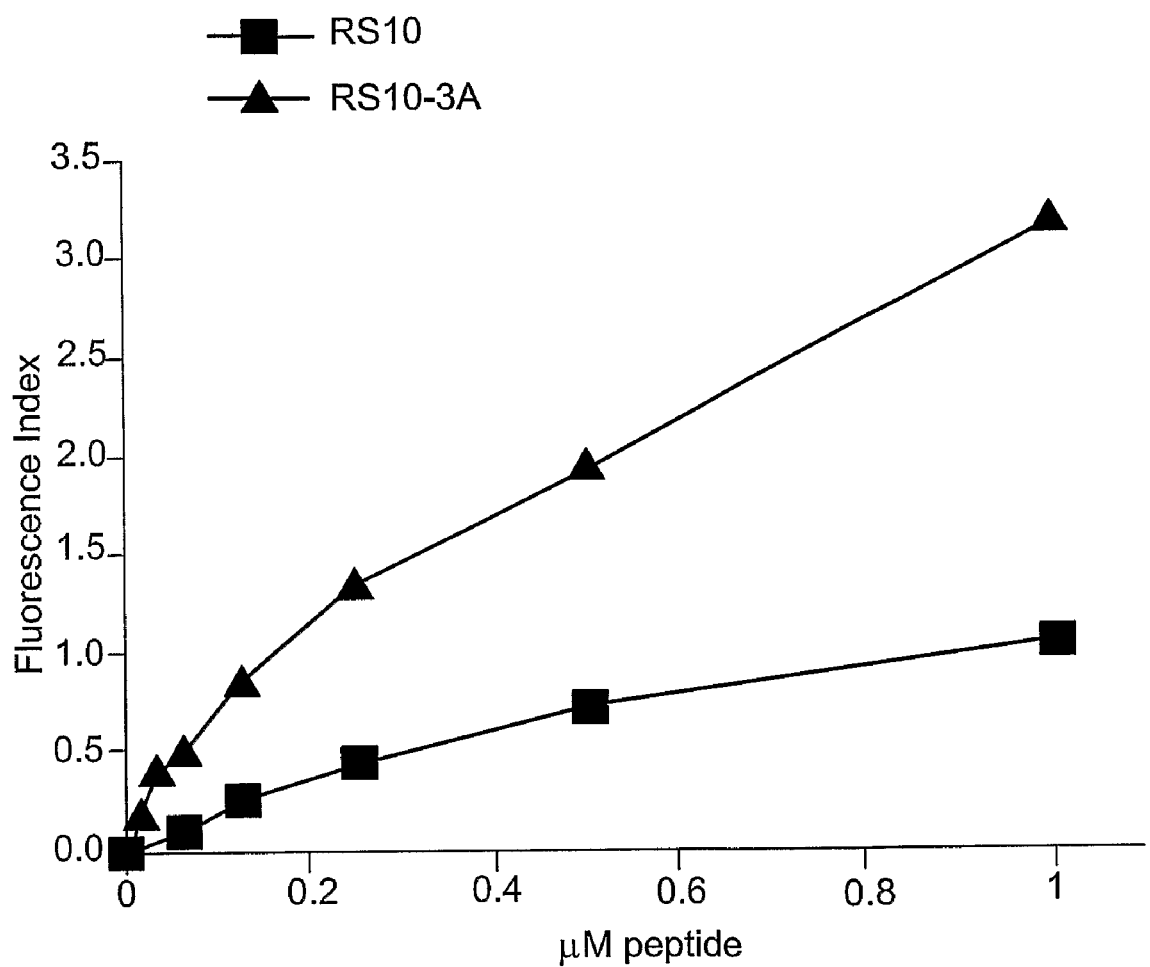
FIG. 4 depicts the fluorescence index at different concentrations of RS10 peptide (squares) or RS10-3A mutant peptide (triangles).
Figure 6:
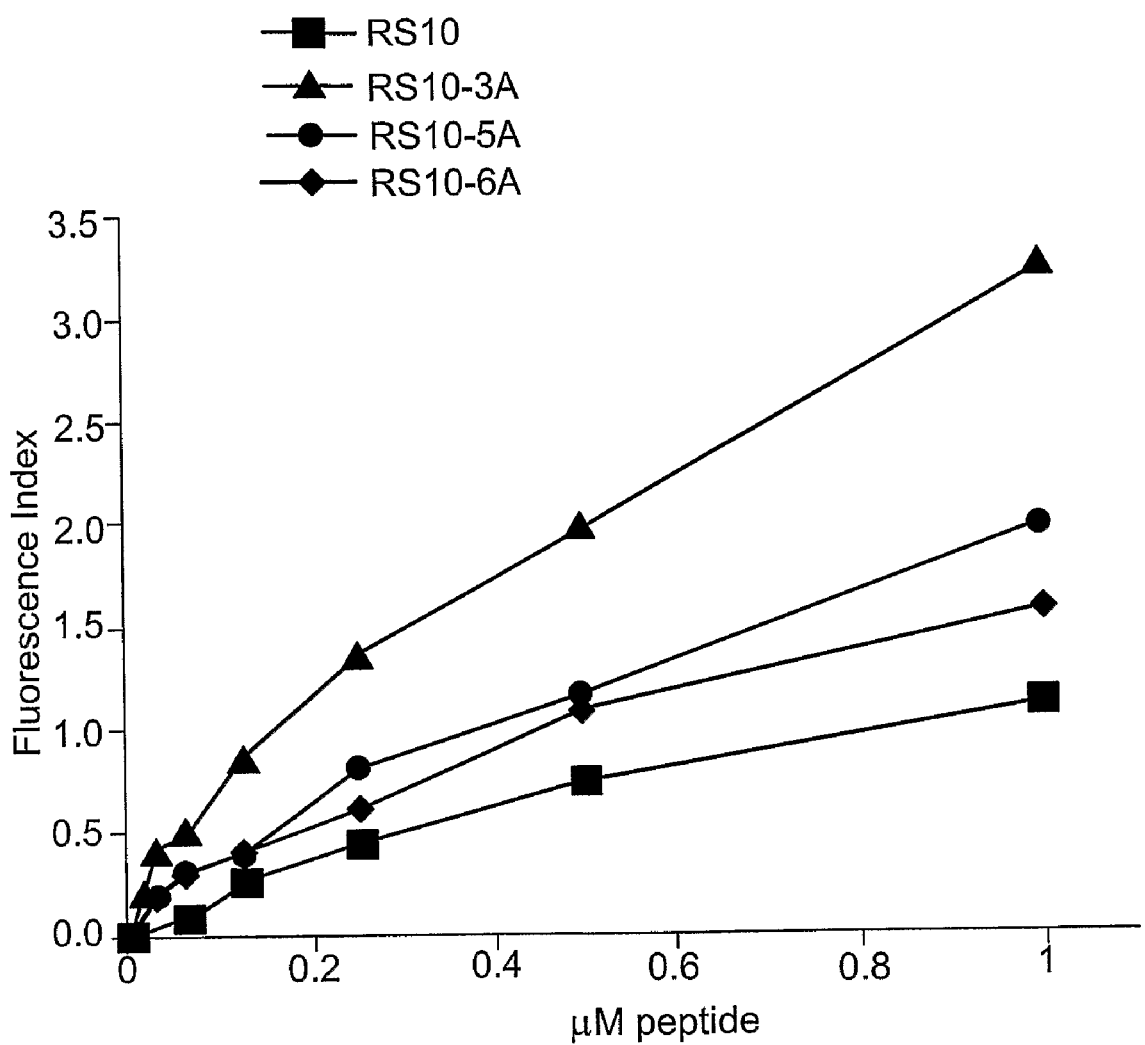
FIG. 6 depicts the fluorescence index at different concentrations of RS10 peptide (squares), RS10-3A mutant peptide (triangles), RS10-5A mutant peptide (circles), or RA10-6A mutant peptide (diamonds).

To maximize immunogenicity, it is often helpful to modify the sequence of an epitope to increase the affinity for the relevant MHC molecule, in a process that is called epitope enhancement (Berzofsky et al., *Ann. N.Y. Acad. Sci.*, 690, 256-264 (1993), Berzofsky et al., *Ann. N.Y. Acad. Sci.*, 754, 161-168 (1995), Ahlers et al., *Proc. Natl. Acad. Sci. USA*, 94, 10856-10861 (1997), Sarobe et al., *J. Clin. Invest.*, 102, 1239-1248 (1998), Ahlers et al., *J. Clin. Invest.*, 108, 1677-1685 (2001), Berzofsky et al., *Nature Reviews Immunology*, 1, 209-219 (2001), Okazaki et al., *J. Immunol.*, 171, 2548-2555 (2003), Oh et al., *Cancer Research*, 64, 2610-2618 (2004), and Berzofsky et al., *J. Clin. Invest.*, 113, 1515-1525 (2004)). Such improvements in binding affinity can sometimes be achieved by replacement of an amino acid residue causing an adverse interaction with one that has a small, neutral side chain, such as alanine (Berzofsky et al., *Ann. N.Y. Acad. Sci.*, 690, 256-264 (1993), Berzofsky et al., *Ann. N.Y. Acad. Sci.*, 754, 161-168 (1995), Ahlers et al., *Proc. Natl. Acad. Sci. USA*, 94, 10856-10861 (1997), Ahlers et al., *J. Clin. Invest.*, 108, 1677-1685 (2001), and Boehncke et al., *J. Immunol.*, 150, 331-341 (1993)). To screen for such a possibility, a series of peptides with Ala substitutions at each position in RS10 is synthesized and tested for binding to HLA-B7 in a T2-B7 binding assay. The variants with the Ala substitution at positions 3, 5, and 6 (RS10-3A, RS10-5A, and RS10-6A, respectively) show higher binding affinity for HLA-B7 than the natural RS10 peptide (FIGS. 4 and 6). The concentration required for a 50% increase in HLA-B7 expression is decreased from approximately 0.3 µM for RS10 to approximately 0.05 µM for the RS10-3A variant.

Figure 5:
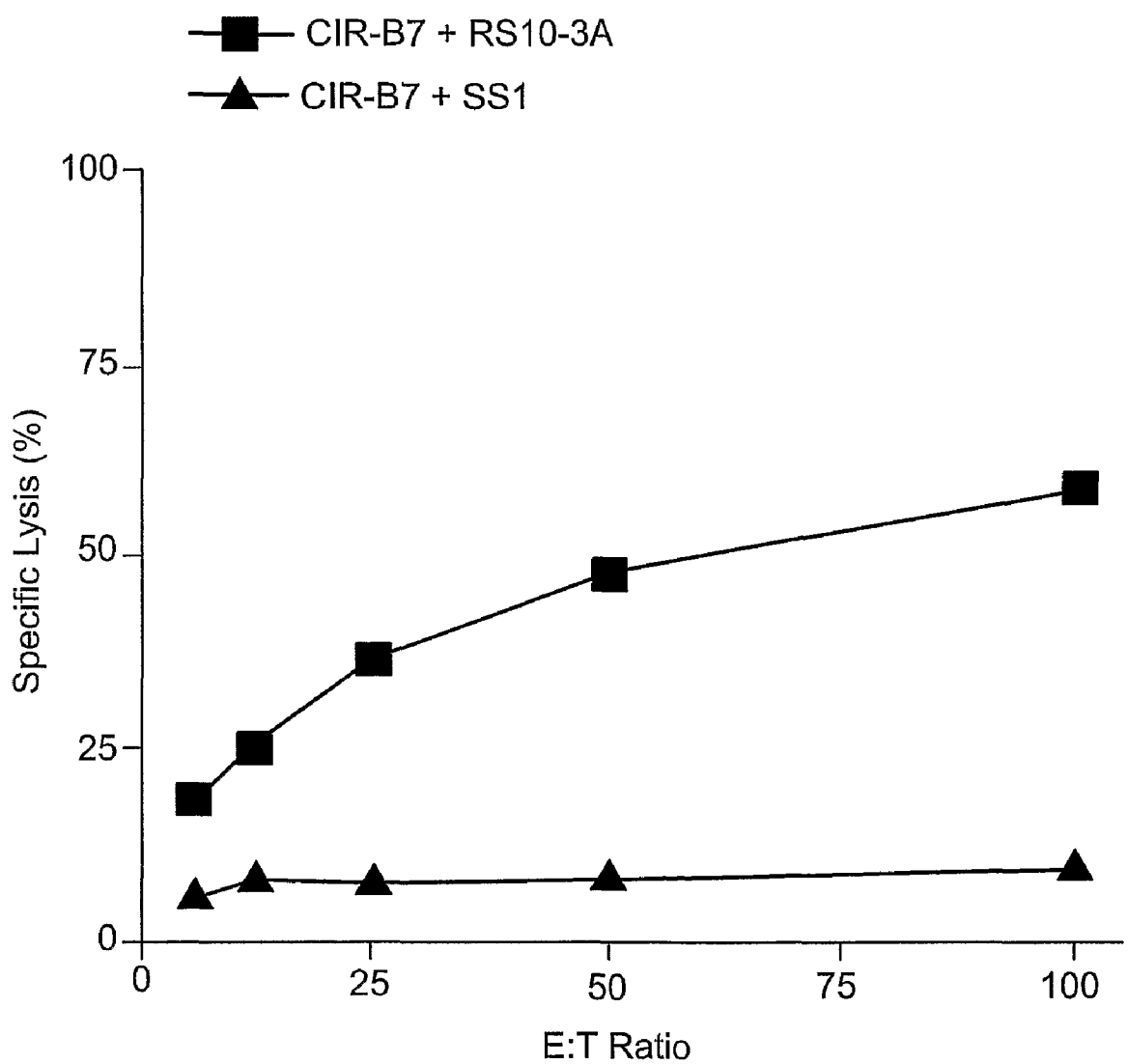
FIG. 5 depicts the CTL lytic activity at different E:T ratios, wherein the effector cells are the CTL generated in Example 2 described herein, and the target cells are C1R-B7 cells pulsed with either RS10-3A peptide (squares) or control peptide (SS1; triangles).

To be sure that the epitope enhanced peptide with increased binding affinity for the HLA molecule has not simultaneously lost recognition by the T cell, the ability of the RS40-specific human CTL to kill C1R-B7 targets pulsed with the RS10-3A peptide is tested as described above. As shown in FIG. 5, the specific killing observed confirms that the enhanced epitope is not so altered in the surface presented to the T cell receptor that it had lost recognition by the human CTL. This enhanced peptide may therefore serve as a candidate vaccine to elicit specific CTL immunity in HLA-B7$^+$ patients with alveolar rhabdomyosarcoma, without the concern that self tolerance could dampen the response, or that the tumor could escape by losing the fusion protein.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated immunogenic peptide comprising the amino acid sequence SPQNSIRHNL (SEQ ID NO: 3), a functional portion or functional variant thereof, or a pharmaceutically acceptable salt thereof, wherein the peptide, or functional portion or functional variant thereof, binds to an MHC Class I molecule, provided that the peptide does not consist of the amino acid sequence TIGNGLSPQNSIRHNLSL (SEQ ID NO: 4) or NPTGTIGNGLSPQNSIRHNLSLH (SEQ ID NO: 5), wherein the functional portion comprises 50% or more of the immunogenic peptide comprising SEQ ID NO: 3, wherein the functional variant comprises one conservative amino acid substitution, and wherein the peptide consists of 8 to 10 amino acids.

2. An immunogenic peptide comprising the amino acid sequence SPX$_1$NX$_2$X$_3$RHNL (SEQ ID NO: 6), wherein X$_1$ is any amino acid except for Gln, X$_2$ is any amino acid except for Ser, and X$_3$ is any amino acid except for Ile, a functional portion, or a pharmaceutically acceptable salt thereof, wherein the peptide or functional portion thereof binds to an MHC Class I molecule, wherein the functional portion comprises 50% or more of the immunogenic peptide comprising SEQ ID NO: 3.

3. The immunogenic peptide of claim 1, wherein the functional variant has enhanced ability to bind to the MHC Class I molecule as compared to a peptide that lacks one conservative amino acid substitution.

4. The immunogenic peptide of claim 1, wherein the MHC Class I molecule is HLA-B7.

5. The immunogenic peptide of claim 1, wherein the immunogenic peptide stimulates cytotoxic T lymphocytes.

6. The immunogenic peptide of claim 5, wherein the immunogenic peptide stimulates cytotoxic T lymphocytes to kill tumor cells.

7. The immunogenic peptide of claim 6, wherein the tumor cells are alveolar rhabdomyosarcoma cells.

8. The immunogenic peptide of claim 2, wherein each of X$_1$, X$_2$ and X$_3$ is independently any small, aliphatic amino acid.

9. The immunogenic peptide of claim 8, wherein X$_1$ is Ser, Thr, or Ala; X$_2$ is Thr or Ala; and X$_3$ is Ser, Thr, or Ala.

10. The immunogenic peptide of claim 2, wherein the peptide is selected from the group consisting of: SPANSIRHNL (SEQ ID NO: 7); SPQNAIRHNL (SEQ ID NO: 8); and SPQNSARHNL (SEQ ID NO: 9).

11. The immunogenic peptide of claim 1, wherein the peptide is SPQNSIRHNL (SEQ ID NO: 3).

12. A fusion protein comprising the immunogenic peptide of claim 1 and an MHC Class I molecule, or a functional portion thereof.

13. The fusion protein of claim 12, wherein the MHC Class I molecule is HLA-B7.

14. A conjugate comprising the immunogenic peptide of claim 1 conjugated to a targeting moiety.

15. A pharmaceutical composition comprising the peptide of claim 1 and a pharmaceutically acceptable carrier.

16. A pharmaceutical composition comprising the fusion protein of claim 12 and a pharmaceutically acceptable carrier.

17. A pharmaceutical composition comprising the conjugate of claim 14 and a pharmaceutically acceptable carrier.

* * * * *

SEQUENCE LISTING

```
<160> NUMBER OF SEQ ID NOS: 9

<210> SEQ ID NO 1
<211> LENGTH: 836
<212> TYPE: PRT
<213> ORGANISM: Homo sapiens

<400> SEQUENCE: 1

Met Thr Thr Leu Ala Gly Ala Val Pro Arg Met Met Arg Pro Gly Pro
1               5                   10                  15

Gly Gln Asn Tyr Pro Arg Ser Gly Phe Pro Leu Glu Val Ser Thr Pro
            20                  25                  30

Leu Gly Gln Gly Arg Val Asn Gln Leu Gly Gly Val Phe Ile Asn Gly
        35                  40                  45

Arg Pro Leu Pro Asn His Ile Arg His Lys Leu Val Glu Met Ala His
    50                  55                  60

His Gly Ile Arg Pro Cys Val Ile Ser Arg Gln Leu Arg Val Ser His
65                  70                  75                  80

Gly Cys Val Ser Lys Ile Leu Cys Arg Tyr Gln Glu Thr Gly Ser Ile
                85                  90                  95

Arg Pro Gly Ala Ile Gly Gly Ser Lys Pro Lys Gln Val Thr Thr Pro
            100                 105                 110

Asp Val Glu Lys Lys Ile Glu Glu Tyr Lys Arg Glu Asn Pro Gly Met
        115                 120                 125

Phe Ser Trp Glu Ile Arg Asp Lys Leu Leu Lys Asp Ala Val Cys Asp
    130                 135                 140

Arg Asn Thr Val Pro Ser Val Ser Ser Ile Ser Arg Ile Leu Arg Ser
145                 150                 155                 160
```

-continued

```
Lys Phe Gly Lys Gly Glu Glu Glu Ala Asp Leu Glu Arg Lys Glu
            165                 170                 175

Ala Glu Glu Ser Glu Lys Lys Ala Lys His Ser Ile Asp Gly Ile Leu
        180                 185                 190

Ser Glu Arg Ala Ser Ala Pro Gln Ser Asp Glu Gly Ser Asp Ile Asp
        195                 200                 205

Ser Glu Pro Asp Leu Pro Leu Lys Arg Lys Gln Arg Arg Ser Arg Thr
210                 215                 220

Thr Phe Thr Ala Glu Gln Leu Glu Glu Leu Glu Arg Ala Phe Glu Arg
225                 230                 235                 240

Thr His Tyr Pro Asp Ile Tyr Thr Arg Glu Glu Leu Ala Gln Arg Ala
                245                 250                 255

Lys Leu Thr Glu Ala Arg Val Gln Val Trp Phe Ser Asn Arg Arg Ala
            260                 265                 270

Arg Trp Arg Lys Gln Ala Gly Ala Asn Gln Leu Met Ala Phe Asn His
        275                 280                 285

Leu Ile Pro Gly Gly Phe Pro Pro Thr Ala Met Pro Thr Leu Pro Thr
    290                 295                 300

Tyr Gln Leu Ser Glu Thr Ser Tyr Gln Pro Thr Ser Ile Pro Gln Ala
305                 310                 315                 320

Val Ser Asp Pro Ser Ser Thr Val His Arg Pro Gln Pro Leu Pro Pro
                325                 330                 335

Ser Thr Val His Gln Ser Thr Ile Pro Ser Asn Pro Asp Ser Ser Ser
            340                 345                 350

Ala Tyr Cys Leu Pro Ser Thr Arg His Gly Phe Ser Ser Tyr Thr Asp
        355                 360                 365

Ser Phe Val Pro Pro Ser Gly Pro Ser Asn Pro Met Asn Pro Thr Ile
    370                 375                 380

Gly Asn Gly Leu Ser Pro Gln Asn Ser Ile Arg His Asn Leu Ser Leu
385                 390                 395                 400

His Ser Lys Phe Ile Arg Val Gln Asn Glu Gly Thr Gly Lys Ser Ser
                405                 410                 415

Trp Trp Met Leu Asn Pro Glu Gly Gly Lys Ser Gly Lys Ser Pro Arg
            420                 425                 430

Arg Arg Ala Ala Ser Met Asp Asn Asn Ser Lys Phe Ala Lys Ser Arg
        435                 440                 445

Ser Arg Ala Ala Lys Lys Lys Ala Ser Leu Gln Ser Gly Gln Glu Gly
    450                 455                 460

Ala Gly Asp Ser Pro Gly Ser Gln Phe Ser Lys Trp Pro Ala Ser Pro
465                 470                 475                 480

Gly Ser His Ser Asn Asp Asp Phe Asp Asn Trp Ser Thr Phe Arg Pro
                485                 490                 495

Arg Thr Ser Ser Asn Ala Ser Thr Ile Ser Gly Arg Leu Ser Pro Ile
            500                 505                 510

Met Thr Glu Gln Asp Asp Leu Gly Glu Gly Asp Val His Ser Met Val
        515                 520                 525

Tyr Pro Pro Ser Ala Ala Lys Met Ala Ser Thr Leu Pro Ser Leu Ser
    530                 535                 540

Glu Ile Ser Asn Pro Glu Asn Met Glu Asn Leu Leu Asp Asn Leu Asn
545                 550                 555                 560

Leu Leu Ser Ser Pro Thr Ser Leu Thr Val Ser Thr Gln Ser Ser Pro
                565                 570                 575

Gly Thr Met Met Gln Gln Thr Pro Cys Tyr Ser Phe Ala Pro Pro Asn
```

-continued

```
                580                 585                 590
Thr Ser Leu Asn Ser Pro Ser Pro Asn Tyr Gln Lys Tyr Thr Tyr Gly
        595                 600                 605
Gln Ser Ser Met Ser Pro Leu Pro Gln Met Pro Ile Gln Thr Leu Gln
        610                 615                 620
Asp Asn Lys Ser Ser Tyr Gly Gly Met Ser Gln Tyr Asn Cys Ala Pro
625                 630                 635                 640
Gly Leu Leu Lys Glu Leu Leu Thr Ser Asp Ser Pro His Asn Asp
                645                 650                 655
Ile Met Thr Pro Val Asp Pro Gly Val Ala Gln Pro Asn Ser Arg Val
        660                 665                 670
Leu Gly Gln Asn Val Met Met Gly Pro Asn Ser Val Met Ser Thr Tyr
        675                 680                 685
Gly Ser Gln Ala Ser His Asn Lys Met Met Asn Pro Ser Ser His Thr
        690                 695                 700
His Pro Gly His Ala Gln Gln Thr Ser Ala Val Asn Gly Arg Pro Leu
705                 710                 715                 720
Pro His Thr Val Ser Thr Met Pro His Thr Ser Gly Met Asn Arg Leu
                725                 730                 735
Thr Gln Val Lys Thr Pro Val Gln Val Pro Leu Pro His Pro Met Gln
                740                 745                 750
Met Ser Ala Leu Gly Gly Tyr Ser Ser Val Ser Ser Cys Asn Gly Tyr
        755                 760                 765
Gly Arg Met Gly Leu Leu His Gln Glu Lys Leu Pro Ser Asp Leu Asp
        770                 775                 780
Gly Met Phe Ile Glu Arg Leu Asp Cys Asp Met Glu Ser Ile Ile Arg
785                 790                 795                 800
Asn Asp Leu Met Asp Gly Asp Thr Leu Asp Phe Asn Phe Asp Asn Val
                805                 810                 815
Leu Pro Asn Gln Ser Phe Pro His Ser Val Lys Thr Thr His Ser
                820                 825                 830
Trp Val Ser Gly
        835

<210> SEQ ID NO 2
<211> LENGTH: 3200
<212> TYPE: DNA
<213> ORGANISM: Homo sapiens

<400> SEQUENCE: 2
ccgtttcgcc ttcacctgga tataatttcc gagcgaagtg cccccaggat gaccacgctg      60
gccggcgctg tgcccaggat gatgcggccg ggccgggggc agaactaccc gcgtagcggg     120
ttcccgctgg aagtgtccac tcccctcggc cagggccgcg tcaaccagct cggcggcgtt     180
tttatcaacg gcaggccgct gcccaaccac atccgccaca gatcgtggga gatgcccac      240 cacggcatcc ggccctgcgt catctcgcgc cagctgcgcg tgtcccacgg ctgcgtctcc     300
aagatcctgt gcaggtacca ggagactggc tccatacgtc ctggtgccat cggcggcagc     360
aagcccaagc aggtgacaac gcctgacgtg gagaagaaaa ttgaggaata caaaagagag     420
aacccgggca tgttcagctg ggaaatccga gacaaattac tcaaggacgc ggtctgtgat     480
cgaaacaccg tgccgtcagt gagttccatc agccgcatcc tgagaagtaa attcgggaaa     540
ggtgaagagg aggaggccga cttggagagg aaggaggcag aggaaagcga gaagaaggcc     600
aaacacagca tcgacggcat cctgagcgag cgagcctcag caccccaatc agatgaaggc     660
```

```
tctgatattg actctgaacc agatttacca ctaaagagga acagcgcag aagccgaacc      720
accttcacag cagaacagct ggaggaactg gagcgtgctt ttgagagaac tcattaccct     780
gacatttata ctagggagga actggcccag agggcgaagc tcaccgaggc ccgagtacag     840
gtctggttta gcaaccgccg tgcaagatgg aggaagcaag ctggggccaa tcaactgatg     900
gctttcaacc atctcattcc cgggggttc cctcccactg ccatgccgac cttgccaacg      960
taccagctgt cggagacctc ttaccagccc acatctattc cacaagctgt gtcagatccc    1020
agcagcaccg ttcacagacc tcaaccgctt cctccaagca ctgtacacca aagcacgatt    1080
ccttccaacc cagacagcag ctctgcctac tgcctcccca gcaccaggca tggattttcc    1140
agctatacag acagctttgt gcctccgtcg gggccctcca acccatgaa ccccaccatt     1200
ggcaatggcc tctcacctca gaattcaatt cgtcataatc tgtccctaca cagcaagttc    1260
attcgtgtgc agaatgaagg aactggaaaa agttcttggt ggatgctcaa tccagagggt    1320
ggcaagagcg ggaaatctcc taggagaaga gctgcatcca tggacaacaa cagtaaattt    1380
gctaagagcc gaagccgagc tgccaagaag aaagcatctc tccagtctgg ccaggagggt    1440
gctggggaca gccctggatc acagttttcc aaatggcctg caagccctgg ctctcacagc    1500
aatgatgact tgataactg gagtacattt cgccctcgaa ctagctcaaa tgctagtact     1560
attagtggga gactctcacc cattatgacc gaacaggatg atcttggaga aggggatgtg    1620
cattctatgg tgtacccgcc atctgccgca aagatggcct ctactttacc cagtctgtct    1680
gagataagca atcccgaaaa catggaaaat cttttggata tctcaacct tctctcatca     1740
ccaacatcat taactgtttc gacccagtcc tcacctggca ccatgatgca gcagacgccg    1800
tgctactcgt ttgcgccacc aaacaccagt ttgaattcac ccagcccaaa ctaccaaaaa    1860
tatacatatg gccaatccag catgagccct ttgccccaga tgcctataca aacacttcag    1920
gacaataagt cgagttatgg aggtatgagt cagtataact gtgcgcctgg actcttgaag    1980
gagttgctga cttctgactc tcctccccat aatgacatta tgacaccagt tgatcctggg    2040
gtagcccagc ccaacagccg ggttctgggc cagaacgtca tgatgggccc taattcggtc    2100
atgtcaacct atggcagcca ggcatctcat aacaaaatga tgaatcccag ctcccatacc    2160
caccctggac atgctcagca gacatctgca gttaacgggc gtcccctgcc ccacacggta    2220
agcaccatgc cccacacctc gggtatgaac cgcctgaccc aagtgaagac acctgtacaa    2280
gtgcctctgc ccaccccat gcagatgagt gccctggggg ctactcctc cgtgagcagc      2340
tgcaatggct atggcagaat gggccttctc caccaggaga agctcccaag tgacttggat    2400
ggcatgttca ttgagcgctt agactgtgac atggaatcca tcattcggaa tgacctcatg    2460
gatggagata cattggattt taactttgac aatgtgttgc ccaaccaaag cttcccacac    2520
agtgtcaaga caacgacaca tagctgggtg tcaggctgag ggttagtgag caggttacac    2580
ttaaaagtac ttcagattgt ctgacagcag gaactgagag aagcagtcca aagatgtctt    2640
tcaccaactc cctttttagtt ttcttggtta aaaaaaaaa acaaaaaaaa aaaccctcct    2700
ttttttcctttt cgtcagactt ggcagcaaag acatttttcc tgtacaggat gtttgcccaa  2760
tgtgtgcagg ttatgtgctg ctgtagataa ggactgtgcc attggaaatt tcattacaat    2820
gaagtgccaa actcactaca ccatataatt gcagaaaaga ttttcagatc ctggtgtgct    2880
ttcaagttttt gtatataagc agtagataca gattgtattt gtgtgtgttt ttggttttt    2940
taaatatcca attggtccaa ggaaagttta tactcttttt gtaatactgt gatgggcctc    3000
```

-continued

```
atgtcttgat aagttaaact tttgtttgta ctacctgttt tctgcggaac tgacggatca    3060
caaagaactg aatctccatt ctgcatctcc attgaacagc cttggacctg ttcacgttgc    3120
cacagaattc acatgagaac caagtagcct gttatcaatc tgctaaatta atggacttgt    3180
taaacttttg gaaaaaaaag                                                3200
```

```
<210> SEQ ID NO 3
<211> LENGTH: 10
<212> TYPE: PRT
<213> ORGANISM: Artificial Sequence
<220> FEATURE:
<223> OTHER INFORMATION: Synthetic

<400> SEQUENCE: 3

Ser Pro Gln Asn Ser Ile Arg His Asn Leu
1               5                   10

<210> SEQ ID NO 4
<211> LENGTH: 18
<212> TYPE: PRT
<213> ORGANISM: Artificial Sequence
<220> FEATURE:
<223> OTHER INFORMATION: Synthetic

<400> SEQUENCE: 4

Thr Ile Gly Asn Gly Leu Ser Pro Gln Asn Ser Ile Arg His Asn Leu
1               5                   10                  15

Ser Leu

<210> SEQ ID NO 5
<211> LENGTH: 23
<212> TYPE: PRT
<213> ORGANISM: Artificial Sequence
<220> FEATURE:
<223> OTHER INFORMATION: Synthetic

<400> SEQUENCE: 5

Asn Pro Thr Gly Thr Ile Gly Asn Gly Leu Ser Pro Gln Asn Ser Ile
1               5                   10                  15

Arg His Asn Leu Ser Leu His
            20

<210> SEQ ID NO 6
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: X is any amino acid except for Q.
<220> FEATURE:
<221> NAME/KEY: misc_feature
<222> LOCATION: (5)..(5)
<223> OTHER INFORMATION: X is any amino acid except for S.
<220> FEATURE:
<221> NAME/KEY: misc_feature
<222> LOCATION: (6)..(6)
<223> OTHER INFORMATION: X is any amino acid except for I.

<400> SEQUENCE: 6

Ser Pro Xaa Asn Xaa Xaa Arg His Asn Leu
1               5                   10

<210> SEQ ID NO 7
```

```
<211> LENGTH: 10
<212> TYPE: PRT
<213> ORGANISM: Artificial Sequence
<220> FEATURE:
<223> OTHER INFORMATION: Synthetic

<400> SEQUENCE: 7

Ser Pro Ala Asn Ser Ile Arg His Asn Leu
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic

<400> SEQUENCE: 8

Ser Pro Gln Asn Ala Ile Arg His Asn Leu
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic

<400> SEQUENCE: 9

Ser Pro Gln Asn Ser Ala Arg His Asn Leu
1               5                   10
```